United States Patent
Yuasa et al.

(10) Patent No.: US 12,257,328 B2
(45) Date of Patent: Mar. 25, 2025

(54) OIL-BASED SOLID COSMETIC

(71) Applicant: JO Cosmetics Co., Ltd., Tokyo (JP)

(72) Inventors: Ryuta Yuasa, Tokyo (JP); Kazuki Uchida, Kanagawa (JP); Yusuke Akizuki, Tokyo (JP)

(73) Assignee: JO Cosmetics Co., Ltd., Tokyo (JP)

( * ) Notice: Subject to any disclaimer, the term of this patent is extended or adjusted under 35 U.S.C. 154(b) by 0 days.

(21) Appl. No.: 17/268,620

(22) PCT Filed: Aug. 6, 2019

(86) PCT No.: PCT/JP2019/031004
§ 371 (c)(1),
(2) Date: Feb. 16, 2021

(87) PCT Pub. No.: WO2020/039917
PCT Pub. Date: Feb. 27, 2020

(65) Prior Publication Data
US 2021/0169756 A1    Jun. 10, 2021

(30) Foreign Application Priority Data
Aug. 18, 2018    (JP) ................. 2018-153756

(51) Int. Cl.
*A61K 8/25*    (2006.01)
*A61K 8/19*    (2006.01)
*A61K 8/31*    (2006.01)
*A61K 8/37*    (2006.01)
*A61Q 1/14*    (2006.01)

(52) U.S. Cl.
CPC .................. *A61K 8/25* (2013.01); *A61K 8/19* (2013.01); *A61K 8/31* (2013.01); *A61K 8/37* (2013.01); *A61Q 1/14* (2013.01)

(58) Field of Classification Search
None
See application file for complete search history.

(56) References Cited

U.S. PATENT DOCUMENTS

| | | | | |
|---|---|---|---|---|
| 5,661,119 A * | 8/1997 | Hersh | ................... | A61K 8/9794 510/462 |
| 5,702,714 A * | 12/1997 | Goss | ...................... | A61K 8/925 424/401 |
| 5,922,359 A * | 7/1999 | Youssefyeh | ............... | A61K 8/27 424/570 |
| 6,187,324 B1 * | 2/2001 | Ogi | ...................... | A61K 8/0212 424/78.05 |
| 6,277,797 B1 * | 8/2001 | Glenn, Jr. | ................. | A61K 8/26 510/130 |
| 7,776,347 B2 | 8/2010 | Kerschner et al. | | |
| 8,298,990 B2 * | 10/2012 | Wu | ........................ | A01N 43/90 504/116.1 |
| 2005/0123574 A1 * | 6/2005 | Abbas | ....................... | A61K 8/26 424/401 |
| 2005/0180942 A1 * | 8/2005 | Shimizu | .................. | A61K 8/342 424/70.31 |
| 2007/0207937 A1 * | 9/2007 | Fonolla Moreno | ...... | A61K 8/86 510/136 |
| 2009/0088360 A1 * | 4/2009 | Wenzel | ................... | A61K 8/365 510/159 |
| 2009/0130042 A1 * | 5/2009 | Moaddel | ................. | A61K 8/375 424/65 |
| 2015/0328103 A1 * | 11/2015 | Guerra | .................. | A61K 8/8147 514/164 |
| 2016/0120778 A1 * | 5/2016 | Greco | ....................... | A61K 8/37 514/512 |
| 2017/0049668 A1 * | 2/2017 | Fernandez | .............. | A61K 8/442 |
| 2017/0252272 A1 * | 9/2017 | George | ................. | A61K 8/0216 |
| 2018/0265807 A1 * | 9/2018 | Morimoto | ................ | C11D 1/74 |
| 2018/0296451 A1 * | 10/2018 | O'Neil | ..................... | A61K 8/416 |
| 2019/0328641 A1 * | 10/2019 | Kelada | .................... | A61K 8/365 |

FOREIGN PATENT DOCUMENTS

| | | | | |
|---|---|---|---|---|
| EP | 309795 A | * | 4/1989 | ............. C09D 9/005 |
| EP | 437956 A | * | 7/1991 | ............. A61K 8/046 |
| JP | 2001213726 A | | 8/2001 | |
| JP | 2002302421 A | | 10/2002 | |
| JP | 2002322029 A | | 11/2002 | |
| JP | 2004346062 A | | 12/2004 | |
| JP | 2006069933 A | | 3/2006 | |
| JP | 2008195614 A | | 8/2008 | |
| JP | 2012206974 A | | 10/2012 | |
| JP | 2013091609 A | * | 5/2013 | |
| JP | 2014105199 A | | 6/2014 | |
| JP | 2015020974 A | * | 2/2015 | |
| JP | 2017095375 A | | 6/2017 | |
| KR | 20070080644 A | * | 8/2007 | |
| KR | 20110079133 A | * | 7/2011 | |
| KR | 2015087608 A | * | 7/2015 | |

(Continued)

OTHER PUBLICATIONS

Google translation KR 2007/0080644, printed 2021 (Year: 2021).*

(Continued)

*Primary Examiner* — Ileana Popa
*Assistant Examiner* — Alissa Prosser
(74) *Attorney, Agent, or Firm* — CAHN & SAMUELS, LLP

(57) ABSTRACT

A solid cosmetic which contains 1 to 30% by mass of (A) a solid oil component having a melting point of 50 to 120° C., 50 to 95% by mass % of (B) a liquid oil component, 3 to 40% by mass % of (C) a nonionic surfactant having an HLB value of 5 to 13, 0.1 to 20% by mass % of (D) a powder having a volume average particle diameter of 1 to 200 μm, and 0.1 to 10% by mass of (E) fumed silica is excellent in cleansing property, washing-off property and refreshing feeling after washing, and is also excellent in quality stability such as appearance and uniformity of composition.

2 Claims, No Drawings

(56) References Cited

FOREIGN PATENT DOCUMENTS

| WO | 2005039516 A1 | 5/2005 |
|---|---|---|
| WO | 2016058180 A1 | 4/2016 |
| WO | 2018131534 A1 | 7/2018 |

OTHER PUBLICATIONS

SpecialChem, Technical Data Sheet Nikkol GO-430 (PEG-30 sorbitan tetraoleate), printed 2021: https://cosmetics.specialchem.com/product/i-nikkol-nikkol-go-430 (Year: 2021).*
Wikipedia "Fumed silica" last edited Mar. 31, 2021; https://en.wikipedia.org/wiki/Fumed_silica (Year: 2021).*
Google translation KR 2011-0079133 A, printed 20222 (Year: 2022).*
Balasubramanian et al. "Oleogel: a promising base for transdermal formulations," Asian Journal of Pharmaceutics, Jan.-Mar. 2012 (Year: 2012).*
Degussa Product Information for "Aerosil® 200," Jul. 2004 (Year: 2004).*
Whitby et al. "Understanding the role of hydrogen bonding in the aggregation of fumed silica particles in triglyceride solvents," Journal of Colloid and Interface Science 527:1-9, 2018 (Year: 2018).*
Google translation KR 2015-0087608 A, printed 2023 (Year: 2023).*
English Abstract for JP2002322029A, Nov. 8, 2002.
English Abstract for JP2006069933A, Mar. 16, 2006.
English Abstract for JP2008195614A, Aug. 28, 2008.
English Abstract for JP2014105199A, Jun. 9, 2014.
English Abstract for WO2005039516A1, May 6, 2005.
English Abstract for WO2016058180A1, Apr. 21, 2016.
English Abstract for WO2018131534A1, Jul. 19, 2018.
English Abstract for JP2002302421A, Oct. 18, 2002.
English Abstract for JP2001213726A, Aug. 7, 2001.
English Abstract for JP2012206974A, Oct. 25, 2012.
English translation of International Written Opinion for Application No. PCT/JP2019/031004, May 2019.
English Abstract for JP2004346062 A, Dec. 9, 2004.

* cited by examiner

OIL-BASED SOLID COSMETIC

This application is a U.S. national stage application of PCT/JP2019/031004 filed on 6 Aug. 2019 and claims priority to Japanese patent document 2018-153756 filed on 18 Aug. 2018, the entireties of which are incorporated herein by reference.

TECHNOLOGICAL FIELD

This invention relates to an oil-based solid cosmetic. More specifically, the present invention relates to an oil-based solid cosmetic suitable as a cleansing cosmetic.

BACKGROUND TECHNOLOGY

In recent years, a product having both water resistance and oil resistance is developed in a makeup cosmetic such as a lip stick, a foundation, an eye shadow, and a mascara, and a long-lasting property of makeup is remarkably improved. Therefore, in the case of cleansing a makeup (i.e. a cosmetic film on the skin) of the makeup cosmetic, an oil-based cleansing cosmetic having good compatibility with the makeup, and excellent in property of removing stains such as keratin and sebum is used. Examples of the oil-based cleansing cosmetic include a cleansing oil, a gel-like cleansing agent, a cleansing cream, etc. Of these, an oil-based cleansing cosmetic in a solid form at ordinary (room) temperature has features that it does not drip when applied to the makeup, and it is easy to massage when applied to the makeup. Hence, the oil-based solid cleansing cosmetic has been earnestly developed.

Patent Document 1 discloses that a stick-like cleansing cosmetic excellent in properties such as removal of stains on the skin and removal of stains or pore-clogging debris in the skin can be obtained by blending (a) a wax having a melting point of 30 to 60° C., (b) a wax having a melting point of 61 to 110° C., (c) an oil component in a liquid state at normal temperature, and (d) a powder component. However, Patent Document 1 μmerely evaluates a property of removing stains on the skin. It discloses nothing about cleansing a makeup made by a makeup cosmetic. Further, there is no disclosure about washing the cleansing cosmetic off with water or lukewarm water.

Patent Document 2 discloses that an oil-based solid cleansing cosmetic using a solid oil having a high melting point, a liquid oil and a nonionic surfactant does not drip when used, has a smooth and soft feeling of use, and is excellent in compatibility with stains and refreshing feeling after washing it off. Further, Patent Document 3 discloses that an oil-based solid cleansing cosmetic containing (A) a hydrocarbon oil having a high melting point, (B) a liquid oil containing an ester oil as an essential component, and (C) a nonionic surfactant having an HLB value of 5 to 13 is well compatible with a makeup, has an excellent cleansing property, and is excellent in feeling of use such as refreshing feeling after washing.

However, since the oil-based solid cleansing cosmetic is an oily form containing a solid oil, it is not still satisfactory in refreshing feeling after washing, and further improvement of cleansing property (i.e. easiness of removing a makeup) is also desired.

On the other hand, Patent Document 4 discloses that an oil-based solid cosmetic containing, as a solid oil component, an ethylene propylene copolymer, a specific ester oil and fumed silica is excellent in a long-lasting property of makeup, a gloss and a feeling of use. However, Patent Document 4 μmerely discloses that the oil-based solid cosmetic is used for a product such as an eye cream, a lip stick and a lip gloss. It discloses nothing about use of the oil-based solid cosmetic as a cleansing cosmetic.

PRIOR ART DOCUMENT

Patent Document

Patent Document 1: Japanese Patent Laid-Open No. 2002-302421
Patent Document 2: Japanese Patent Laid-Open No. 2001-213726
Patent Document 3: Japanese Patent Laid-Open No. 2012-206974
Patent Document 4: Japanese Patent Laid-Open No. 2006-69933

SUMMARY OF THE INVENTION

Problems to be Solved by the Invention

The present invention has been completed under such a background art. The present invention aims to provide an oil-based solid cosmetic that is excellent in cleansing property, washing-off property, refreshing feeling after washing, and quality stability, while maintaining the foregoing properties peculiar to the conventional oil-based solid cleansing cosmetics.

Means Used to Solve the Problem

The present inventors have intensively studied to solve the above problems, and have found that an oil-based solid cosmetic containing a powder, fumed silica, a solid oil component having a high melting point, a liquid oil and a nonionic surfactant having a specific HLB value, which contains the powder and the fumed silica within a specific ratio satisfies the above requirements. The present invention has been completed based on such knowledge.

Thus, the present invention provides an oil-based solid cosmetic comprising: 1 to 30% by mass of (A) a solid oil component having a melting point of 50 to 120° C., 50 to 95% by mass of (B) a liquid oil component, 3 to 40% by mass of (C) a nonionic surfactant having an HLB value of 5 to 13, 0.1 to 10% by mass of (D) a powder having a volume average-particle diameter of 1 to 200 m, and 0.01 to 10% by mass of (E) fumed silica, wherein the term "% by mass" is in terms of the whole amount of the cosmetic.

The oil-based solid cosmetic of the present invention does not drip when used because of its solid form, has a high cleansing power and a high massage effect, is excellent in washing-off property and refreshing feeling after washing, and is excellent in quality stability.

DETAILED DESCRIPTION OF THE INVENTION (A: Solid Oil Component)

The solid oil component used as the component (A) is an oil that is a solid at ordinary temperature (25° C.) having a melting point of 50 to 120° C., preferably 55 to 105° C., more preferably 60 to 100° C. Here, the melting point of the solid oil component can be measured according to the second method of the melting point measurement method which is a general test method defined in Japanese Standards of Quasi-drug Ingredients. When the melting point is excessively low, the liquid oil used as the component (B) cannot be uniformly solidified, and the composition may be liquefied by vibration or impact added during transportation thereof or when carried with a user, and it makes difficult to maintain a shape of the solid due to a poor shape retention property. On the contrary, when the melting point is excessively high, the composition becomes hard and it becomes difficult to take an appropriate amount of the composition from a container with a finger when the composition is used as a cosmetic, that is, the composition becomes poor in taking-with-finger property. In addition, oxidation deterioration of the component (B) and the component (C) tends to be caused due to an operation at a high temperature necessary for melting the composition.

Examples of the solid oil component include hydrocarbon-based waxes such as paraffin wax, polyethylene wax, ethylene-propylene copolymer, microcrystalline wax, ceresin, ozokerite, and Fischer-Tropsch wax; Japan wax; carnauba wax; candelilla wax; rice wax; beeswax; hydrogenated jojoba oil; hardened oil; higher alcohol; silicone wax; and the like.

Examples of commercial products used as the solid oil component include paraffin waxes such as PARAFFIN WAX 135, PARAFFIN WAX 140, PARAFFIN WAX 150, and HNP-11 any of which is available from Nippon Seiro Co. Ltd.; microcrystalline waxes such as HNP-9, HI-MIC-2065, HI-MIC-1070, HI-MIC-1080, HI-MIC-1090, and HNP-070 any of which is available from Nippon Seiro Co. Ltd, and MULTIWAX W-445 available from Sonneborn, LLC.; polyethylene waxes such as PERFORMALMALEN 400, PERFORMALEN 500, PERFORMALENE 655 any of which is available from NEW PHASE TECHNOLOGIES Inc.; synthetic waxes (Fischer-Tropsch wax) such as CIREBELLE 108 and CIREBELLE 305 both of which are available from CIREBELLE Inc.; candelilla waxes such as Purified candelilla wax NO. 1 and Candelilla NC1630 both of which are available from Cerarica NODA Co., Ltd., Purified candelilla wax CG-7 and Purified candelilla wax SR-3 both of which are available from Yokozeki Oil and Fat Co., Ltd., Refined candelilla Wax CG-7 and Refined candelilla Wax SR-3 both of which are available from Japan Natural Products, and High melting point candelilla wax FR100 available from Japan Natural Products Co., Ltd; and the like.

The oil-based solid cleansing cosmetic is largely different from oil-based solid cosmetics that are used as a makeup cosmetic such as a lip stick in that it is a composition having a large volume. Hence, it is necessary to maintain the composition in a molten state over a long period of time when filled in a predetermined container. Therefore, the solid oil component is preferably a wax excellent in stability against oxidation that may be caused upon heating. Specifically, a hydrocarbon wax is preferably used. In particular, a polyethylene wax or Fischer-Tropsch wax is preferred.

The component (A) may a single compound or a combination of two or more kinds of compounds. The content of the component (A) is 1 to 30% by mass, preferably 2 to 20% by mass, more preferably 3 to 15% by mass in terms of the whole oil-based solid cosmetic. When the content of the component (A) is too small, shape retention becomes insufficient, and massage effect is deteriorated due to excessive softness. On the other hand, when excessively large, 0 becomes poor, and when used, spreadability is poor. When a stick-like oil-based solid cleansing cosmetic is produced, it is preferable that the content of the component (A) is 5 to 30% by mass in terms of the whole cosmetic, and thereby, particularly good shape retention property can be obtained.

(B: Liquid Oil Component)

The oil-based solid cosmetic of the present invention contains a liquid oil component (B) in view of compatibility with makeup on the skin and good spreadability when applied to the skin. Here, the term "liquid oil component" means an oil having fluidity at ordinary temperature (25° C.) and/or a semi-solid oil having a melting point of less than 50° C. A volatile oil having a boiling point of less than 260° C. is also included in the "liquid oil component."

The liquid oil component (B) used in the present invention is not particularly limited as long as it is used in conventional cosmetics, and may be any of animal oils, vegetable oils, and synthetic oils. Examples of the liquid oil component include esters such as triethylhexanoin, diisostearyl malate, diglyceryl triisostearate, decaglyceryl decaisostearate, oligomeric ester of dimer acid and dimer diol, pentaerythrityl tetraisostearate, diglyceryl tetraisostearate, cetyl isooctanoate, isopropyl myristate, isopropyl palmitate, octyldodecyl myristate, neopentyl glycol dioctanoate, cholesterol fatty acid ester and jojoba oil; hydrocarbons such as volatile isoparaffin, polybutene, polyisobutylene, heavy liquid isoparaffin, liquid paraffin, alpha-olefin oligomer, squalane, and petrolatum; oils and fats such as olive oil, castor oil, mink oil and macadamia nut oil; fatty acids such as isostearic acid and oleic acid; higher alcohols such as oleyl alcohol and isostearyl alcohol; and silicone oils such as dimethylpolysiloxane having a low polymerization degree, cyclic silicone, dimethylpolysiloxane having a high polymerization degree, methylphenyl polysiloxane, methyltrimethicone, capryltrimethicon, cross-linked organopolysiloxane, and fluorine-modified polysiloxane; fluorine-based oils such as perfluoropolyether; lanolin derivatives such as lanolin, lanolin acetate, lanolin fatty acid isopropyl, and lanolin alcohol; and the like.

The content of the liquid oil component (B) is 50 to 95% by mass in terms of the whole solid cosmetic, preferably 55 to 95% by mass, more preferably 60 to 90% by mass. When the content of the component (B) is too small, the solid cosmetic tends to have poor compatibility with makeup, and massage property is lowered due to poor spreadability. On the contrary, when the content of the component (B) is excessively large, shape retention property is deteriorated, and massage effect is lowered.

(C: Surfactant)

In the present invention, a nonionic surfactant having an HLB value of 5 to 13 is used as the component (C). Here, the term "a nonionic surfactant having an HLB value of 5 to 13" means that the nonionic surfactant is a single nonionic surfactant having an HLB value of 5 to 13, a combination of a plurality of nonionic surfactants having an HLB value in the range or a combination of a plurality of nonionic surfactants having an HLB value of 5 to 13 based on a weighted average HLB value as a result of combining two or more of nonionic surfactants having a different HLB value. Examples of the combination of nonionic surfactants having a different HLB value include a combination of a surfactant having an HLB value of 5 to 13 and a surfactant having an HLB value of less than 5.

Incidentally, the term "HLB" is an index indicating a balance between hydrophilicity and lipophilicity as a value of from 0 to 20. The higher the lipophilicity, the closer to 0, the higher the hydrophilicity, the closer to 20. Regarding a method of determining an HLB value, various methods have conventionally been known. Further, an HLB value is described in catalogs provided by a manufacturer of nonionic surfactant. In the case of using a commercial nonionic surfactant, its HLB value indicates a value described in its catalog provided by the manufacturer. In the case of using a nonionic surfactant which is not a commercial product, its HLB value is determined in accordance with Method of Griffin which is described on page 307 of "Handbook of surfactants" published in 1960 from Sangyo Tosho publishing. The method is represented by the following formula.

*HLB* value=20×total weight of hydrophilic portion/ molecular weight

When the HLB value of the nonionic surfactant is less than 5, even if the oil-based solid cosmetic is applied to makeup on the skin, and then an attempt to wash the makeup off with water or lukewarm water is performed, it is difficult to wash the makeup and the oil-based solid cosmetic off due to poor affinity of the oil-based solid cosmetic for water, and good refreshing feeling after washing cannot be obtained. On the contrary, when the HLB value exceeds 13, the oil-based solid cosmetic cannot be applied well to hydrophobic makeup, and removal of the makeup is insufficient. Of these, when the HLB value is in the range of 6 to 11, property of removing makeup and washing-off property are good. The nonionic surfactant of the component (C) may be a solid or a liquid. Use of a nonionic surfactant being liquid at 25° C. enables it to obtain an oil-based solid cosmetic excellent in makeup-removal property and washing-off property.

Examples of the nonionic surfactant having an HLB value of 5 to 13 or the nonionic surfactant that is used to make a mixture having an HLB value of 5 to 13 by combining a plurality of nonionic surfactants having a different HLB value which are used as the component (C) include polyglycerol fatty acid esters such as polyglyceryl-4 stearate, polyglyceryl-2 oleate, polyglyceryl-2 isostearate and polyglyceryl-10 distearate; polyoxyethylene hydrogenated castor oils such as PEG-10 hydrogenated castor oil and PEG-20 hydrogenated castor oil; polyoxyethylene fatty acid esters such as PEG-2 stearate and PEG-5 stearate; polyoxyethylene alkyl ethers such as ceteth-2, oleth-3 and steareth-6; fatty acid polyoxyethylene alkyl ethers such as steareth-6 stearate, laureth-8 isostearate and steareth-12 stearate; polyoxyethylene fatty acid glyceryl such as PEG-3 glyceryl isostearate, PEG-15 glyceryl triisostearate, PEG-5 glyceryl triisostearate, PEG-10 glyceryl trisostearate, PEG-20 glyceryl triisostearate and PEG-20 glyceryl tristearate; fatty acid polyoxyethylene hydrogenated castor oils such as PEG-15 hydrogenated castor oil isostearate and PEG-20 hydrogenated castor oil triisostearate; sorbitan fatty acid ester, polyoxyethylene sorbitan fatty acid ester, polyoxyethylene polyoxypropylene copolymer, ether of polyoxyethylene polyoxypropylene copolymer and long-chain alcohol, ether of polybutylene glycol polyglycerin copolymer and long-chain alcohol, and the like. Of these, polyoxyethylene fatty acid ester, polyoxyethylene fatty acid glyceryl, fatty acid polyoxyethylene hydrogenated castor oil and fatty acid polyoxyethylene alkyl ether are preferably used in view of the makeup-removal property and the washing-off property.

When the nonionic surfactant used as the component (C) contains a fatty acid residue in its molecule, it is preferably a residue of a fatty acid having 10 to 22 carbon atoms such as myristic acid, palmitic acid, stearic acid, isostearic acid and oleic acid. Of these, the fatty acid residue is preferably a residue of a branched higher fatty that provides a liquid nonionic surfactant and is excellent in oxidation stability. Particularly, an isostearic acid residue is preferred.

Examples of the liquid nonionic surfactant used as the component (C) which is a commercial product include EMALEX RWIS-320 (PEG-20 hydrogenated castor oil triisostearate; Nihon Emulsion Co., Ltd.; HLB 6), EMALEX GWS-305 (PEG-5 glyceryl triisostearate; Nihon Emulsion Co., Ltd.; HLB 3), and UNIOX GT-201S (PEG-20 glyceryl triisostearate; NOF Corporation; HLB 10.4). Examples of the solid nonionic surfactant commercially available include EMALEX GWS-320 (PEG-20 glyceryl tristearate; Nihon Emulsion Co., Ltd.; HLB 8), EMALEX SWS-12 (steareth-12 stearate; Nihon Emulsion Co., Ltd.; HLB 8), and EMALEX 608 (steareth-8; Nihon Emulsion Co., Ltd.; HLB 9).

The content of the component (C) is 3 to 40% by mass, preferably 4 to 35% by mass, more preferably 5 to 30% by mass, particularly preferably 7 to 25% by mass. When the content is too small, makeup-removal property and washing-off property necessary for a cleansing cosmetic are deteriorated. When the content is too large, irritation to the skin is feared.

(D: Powder)

In the present invention, in addition to the above components (A) to (C), a powder is used as the component (D). The powder-has a volume average particle diameter of 1 to 200 μm, preferably 2 to 100 μm, more preferably 5 to 50 μm. Addition of an appropriate amount of the powder having such an average particle diameter contributes to adsorption of makeup-stain to the oil-based solid cosmetic and generation of moderate friction during massage, and also contributes to improvement of makeup-removal property, refreshing feeling after washing and massage effect. When the volume average particle diameter of the powder is excessively small, makeup-removal property and performance of massage cannot be improved. Conversely, when excessively large, stimulation may be felt upon massaging. Further, when the cosmetic is produced, sedimentation of the powder that leads to non-uniform dispersion of the powder is likely to occur. The non-uniform dispersion of the powder leads to deteriorated appearance and deteriorated quality stability of the product.

In the present invention, the volume average particle diameter does not refer to a primary particle diameter, and is measured using a laser diffraction/scattering particle size distribution measuring apparatus such as LA-950 which is manufactured by Horiba, Ltd. and a sample that is obtained by subjecting to an ultrasonic dispersion treatment for 5 μminutes in an aqueous solution of ethanol having 95% by volume. Here, the ultrasonic dispersion treatment is performed at a frequency of 28 kHz using an ultrasonic cleaning machine W-113 which is manufactured by Honda Electric Co. Ltd.

The content of the component (D) is 0.1 to 20% by mass, preferably 0.2 to 15% by mass, more preferably 1 to 10% by mass in terms of the whole cosmetic. When the component (D) is contained in the range, the makeup-removal property and the massage effect are improved The powder of the component (D) is not particularly limited as long as it can be used for cosmetics, and can be used regardless of a material such as organic and inorganic, a shape such as a spherical shape, a needle shape, and a plate shape, and a particle structure such as a porous particle and a non-porous particle. Of these, powders having a porous structure, or a large specific surface area are preferably used due to excellent ability to adsorb makeup-stains.

Examples of the powder used as the component (D) include clay minerals such as talc, muscovite, synthetic mica, phlogopite, synthetic fluorphlogopite, sericite, zeolite, kaolin, bentonite, saponite, hectorite, natural clay, sea mud, and activated clay; inorganic oxides or inorganic salts such as silicic acid, silicic anhydride (silica), magnesium silicate, magnesium aluminum silicate, calcium silicate, barium sulfate, magnesium carbonate, boron nitride, bismuth oxychloride, alumina, zirconium oxide, and hydroxyapatite; organic powders such as silicone powder, silicone elastic powder, polyurethane powder, cellulose powder, nylon powder, silk powder, PMMA powder, starch, polyethylene powder, lauroyl lysine, metal soap, plant powder (sweet nucleating particle, walnut kernel grain, and glucomannan powder); carbon powders such as activated carbon, medicinal carbon, bamboo charcoal; composites composed of these materials and granules composed of these materials.

Of these, when the clay mineral or the carbon powder is used, a cleansing cosmetic that is excellent in makeup-removal property and refreshing feeling after washing can be obtained. Natural clay and sea mud both of which are clay minerals, are not necessarily the same in composition and hue by their producing area, but any of which is a mixture containing kaolin, montmorillonite, mica etc. Examples of the natural clay and the sea mud include Moroccan lava clay, Tanakura clay, Palau white clay, Sparclay (product name) and Tersil (product name) both of which are produced in Brazil, and Clargile (product name) produced in France.

In the present invention, fumed silica is further contained as the component (E). In order to produce a cleansing cosmetic in accordance with a formulation using a solid oil, a step of filling a predetermined container with a mixture of a plurality of ingredients in a uniformly mixed and molten state, subsequently cooling the mixture for solidification thereof is required. In the case of using a mixture that contains the powder of the component (D), uniform dispersion state of the powder can be maintained if the mixture filled in the container is rapidly solidified. For example, in the case of a makeup cosmetic such as a lip stick, a time from the start of filling to solidification is extremely short since the makeup cosmetic has generally only several grams. Hence, there is little risk of impairing dispersibility of the powder contained in the mixture. However, in the case of a cleansing cosmetic, the time from the start of filling to solidification is long even if the container filled with the mixture is cooled by cold air or the like from the outside since the cleansing cosmetic has generally about 100 grams or more. Hence, the powder component may settle out during the time. When the powder component is settled out, the dispersion of the powder component becomes non-uniform, and bias of the content of the powder component in a vertical direction of the cosmetic occurs. As a result, appearance and quality stability of the cosmetic are impaired.

The content of the component (E) is 0.01 to 10% by mass, preferably 0.1 to 5% by mass, more preferably 0.2 to 3% by mass in terms of the whole cosmetic. A ratio of the component (E) to the component (D) [E/D] is preferably 0.01 to 10, more preferably 0.05 to 5. When the content of the component (E) is within the above range, dispersion state of the component (D) contained in the cosmetic is improved, and when the mixture is melted and filled in the production process of the cleansing cosmetic, sedimentation of the component (D) can be effectively suppressed.

The fumed silica used as the component (E) is a fine and amorphous silica, and is a white powder having a fluffy appearance. This is also known as pyrogenic silica. The fumed silica can be obtained by subjecting a raw material such as silicon tetrachloride to high temperature hydrolysis in an oxyhydrogen flame. A specific surface area of the fumed silica is preferably 30 m$^2$/g or more, more preferably 50 to 400 m$^2$/g, particularly preferably 100 to 400 m$^2$/g. When the specific surface area is excessively small, in the production process of an oil-based solid cosmetic, especially an oi-based solid cleansing cosmetic, the sedimentation of the component (D) cannot be sufficiently suppressed when the mixture is melted and filled.

The primary particle diameter of the fumed silica is preferably 50 nm or less, particularly preferably 20 nm or less. The primary particle size can be determined as an average value of diameters in terms of 3,000 to 5,000 particles measured using an electron microscope. The component (E) may be untreated fumed silica exhibiting hydrophilicity or fumed silica subjected to a hydrophobic treatment. Examples of the hydrophobic treatment include dimethyldichlorosilane treatment; trimethylsiloxy treatment using trimethylsilyl chloride or hexamethyldisilazane; octylsilane treatment; dimethylsilicone oil treatment; coating baking treatment using methyl hydrogen polysiloxane; and coating treatment with metal soap. Of these, the untreated fumed silica is preferably used in view of washing-off property.

Examples of commercial products of the component (E) include untreated fumed silica such as AEROSIL 50, AEROSIL 130, AEROSIL 200, AEROSIL 200V, AEROSIL 200 CF, AEROSIL 200 FAD, AEROSIL 300, AEROSIL 300 CF, AEROSIL 380, and AEROSIL 380S any of which is manufactured by Nippon Aerosil Co. Ltd.; and hydrophobic treated materials such as AEROSIL R972, AEROSIL R972V, AEROSIL R972 CF, AEROSIL R974, AEROSIL R976S, AEROSIL RX200, AEROSIL RX300, AEROSIL RY200, AEROSIL R202, AEROSIL R805, AEROSIL R812, AEROSIL RA200H any of which is manufactured by Nippon Aerosil Co. Ltd., CAB-O-SIL and TS530 both of which are available from Cabot Corporation.

The oil-based solid cosmetic may contain a small amount of water as component (F). The content of water is preferably 5% by mass or less in terms of the whole cosmetic, and when it is in the range, nonionic surfactant of the component (C) and water are in a solubilized state, that is, an oily component is present as a dispersion medium, and the component (C) and the water form a reversed micelle. As a result, the nonionic surfactant of component (C) is easily dissolved in an oily phase formed by the component (A) and the component (B), and separation or sedimentation of the component (C) does not occur even in a long-term storage, and storage stability is improved. When the water content is 0.1 to 3% by mass, the effect is remarkable.

The oil-based solid cosmetic of the present invention may contain other components which are used in conventional cosmetics, for example, additives such as other powders except for ones used as the component (D), dyes, oily gelling agents, oil-soluble resins, polyhydric alcohols, lower alcohols, ultraviolet absorbers, ultraviolet scattering agents, humectants, perfumes, antioxidants, antiseptics, defoaming agents, and various kinds of extracts, in a range that the effects of the present invention are not impaired.

The oil-based solid cosmetic has no fluidity at normal temperature (25° C.) and atmospheric pressure (1 atm), and the shape thereof is not particularly limited. Examples of the shape include a stick-like, a rod-like, a plate-shaped, and a shape molded by casting the raw material into a container, and the like. These various cosmetics can be prepared according to conventional methods. For example, after the whole raw materials are heated to a melting point or higher and mixed uniformly, a mixture obtained in a molten state is poured into a predetermined container such as a jar container, dish-like container made of a metal or a resin and so on, and is cooled or allowed to cool to obtain an oil-based solid cosmetic. Also, it can be filled into a stick container to form a stick-like shape.

The oil-based solid cosmetic has properties required for a massage cosmetic in addition to a function for removing a makeup that is necessary for a cleansing cosmetic, that is, moderate viscosity, moderate slip property, and persistence of the moderate slip property. Therefore, the oil-based solid cosmetic of the present invention can be also used as a massage cosmetic in addition to a cleansing cosmetic. When the oil-based solid cosmetic of the present invention is used as a cleansing cosmetic, makeup can be removed by washing it off with water or lukewarm water after the oil-based solid cosmetic is applied to the makeup. Therefore, it is possible to omit a face washing operation using a facial wash agent such as a soap which has been considered necessary in the case of using the conventional oil-based solid cleansing cosmetics. Of course, it can also be used as a cleansing agent for removing stains such as sebum accumulated on the skin which has no makeup.

EXAMPLES

Hereinafter, the present invention will be further described with reference to Examples and Comparative Examples, but the present invention is not limited by these Examples. The content of each ingredient in formulations described below is expressed in % by mass in terms of the whole composition unless otherwise specified.

The evaluation methods of the oil-based solid cosmetic in the following Examples and Comparative Examples are as follows.

(Makeup-removal Property, Washing-off Property, Refreshing Feeling After Washing) product Each of 10 female evaluators having an experience to use a cosmetic applied a commercially available powder foundation (CE-ZANNE UV Foundation EX PLUS available from CEZANNE Corp.) to the skin to make a makeup. Subsequently, the makeup was cleansed with a sample for evaluation. With respect to each evaluation item, each evaluator scored at five levels of 1 to 5 according to the evaluation criteria shown in (1) below, and an average value of scores of the 10 evaluators was calculated. Performance as a cleansing cosmetic was determined according to the four-stage determination criteria shown in (2) below.
(1) Evaluation Criteria
    5: Good
    4: Slightly Good
    3: Cannot say either
    2: Slightly poor
    1: Poor
(2) Four-stage Determination Criteria
    Double Circle: Average Point is 4 to 5
    Single Circle: Average Point is 3 or more and less than 4
    Delta: Average Point is 2 or more and less than 3
    X: Average Point is less than 2
(State of Sedimentation of Powder and State of Color Separation)
A sample for evaluation of 150 g was melted at 80° C. and then was poured into a paper cup having an internal volume of 250 μmL at 70° C., and the content was allowed to cool and solidified at room temperature (25° C.) for 1 hour, and the content was cut vertically with the paper cup by a cutter knife. Then, the cross section was observed to evaluate the state of sedimentation of powder according to the evaluation criteria described below. In the case of using powders having a different color tone each other in combination, the state of color separation was also evaluated.
(Evaluation Criteria of State of Sedimentation of Powder)
    Double Circle: No sedimentation of powder due to uniform dispersion.
    Single Circle: In layers upper than ⅕ from the top of the cross section, there was a part in which the powder content is small.
    Delta: In layers upper than ⅕ from the top of the cross section, the powder was not observed.
    X: In layers upper than ⅓ from the top of the cross section, the powder was not observed.
(Evaluation Criteria of State of Color Separation)
    Double Circle: Same color tone and no color separation over the entire surface.
    Single Circle: In layers upper than ⅕ from the top of the cross section, a part having a slightly different color tone was observed.
    Delta: In layers upper than ⅕ from the top of the cross section, a part having a different color tone was observed.
    X: In layers upper than ⅓ from the top of the cross section, a part having a different color tone was observed.

Examples 1 to 2 and Comparative Examples 1 to 3

(Oil-Based Solid Cleansing Cosmetic)
An oil-based solid cleansing cosmetic of the formulation shown in table 1 was prepared according to the following production procedure. In the formulation, two kinds of nonionic surfactants having a different HLB value as component (C) were used in combination, and an HLB value of the component (C) was 8.6 by the weighted average. The obtained oil-based solid cleansing cosmetic was evaluated according to the methods described above as to makeup-removal property, washing-off property, refreshing feeling after washing, state of sedimentation of powder, and state of color separation. The evaluation results are shown in table 1.
(Production Procedure)
    (1) Components 1 to 7 shown in Table 1 were heated to about 90° C. and mixed uniformly.
    (2) Components 8 to 13 were added to the mixture prepared in the above (1), and then the resultant mixture was uniformly mixed at 90° C.
    (3) The mixture prepared in the above (2) was filled in a jar container at 70° C. in a molten state, and then allowed to cool to obtain an oil-based solid cleansing cosmetic.

TABLE 1

|   | Component (%) | Example 1 | Example 2 | Comparative Example 1 | Comparative Example 2 | Comparative Example 3 |
|---|---|---|---|---|---|---|
| 1 | Polyethylene (✶1) | 7.00 | 7.00 | 7.00 | 7.00 | 7.00 |
| 2 | Caprylic/capric triglyceride | Balance | Balance | Balance | Balance | Balance |
| 3 | Dicaprylylyl carbonate | 12.00 | 12.00 | 12.00 | 12.00 | 12.00 |
| 4 | Purified water | 0.50 | 0.50 | 0.50 | 0.50 | 0.50 |

TABLE 1-continued

|   | Component (%) | Example 1 | Example 2 | Comparative Example 1 | Comparative Example 2 | Comparative Example 3 |
|---|---|---|---|---|---|---|
| 5 | PEG-20 glyceryl triisostearate (HLB: 10.4) (※2) | 12.00 | 12.00 | 12.00 | 12.00 | 12.00 |
| 6 | PEG-5 glyceryl triisostearate (HLB: 3) (※3) | 4.00 | 4.00 | 4.00 | 4.00 | 4.00 |
| 7 | Dextrin palmitate (※4) | | | | | 1.00 |
| 8 | Moroccan lava clay (※5) | 2.00 | 2.00 | | 2.00 | 2.00 |
| 9 | Kaolin (※6) | | 1.00 | | | |
| 10 | Silica (Specific surface area 200 m²/g) (※7) | 1.00 | | 1.00 | | |
| 11 | Dimethicone treated silica (Specific surface area 200 m²/g) (※8) | | 1.00 | | | |
| 12 | Tocopherol | 0.05 | 0.05 | 0.05 | 0.05 | 0.05 |
| 13 | Phenoxyethanol | 0.20 | 0.20 | 0.20 | 0.20 | 0.20 |
| Evaluation | Makeup-removal Property | ◎ | ◎ | Δ | ○ | ○ |
| | Washing-off Property | ◎ | ○ | ○ | ○ | X |
| | Refreshing Feeling After Washing | ◎ | ○ | Δ | ○ | X |
| | State of Sedimentation of Powder | ◎ | ◎ | — | X | Δ |
| | State of Color Separation | — | ◎ | — | — | — |

*1 Product name: PERFORMALENE 500 (New Phase Technology)
*2 Product name: UNIOX GT 20-IS (NOF Corporation.)
*3 Product name: EMALEX GWIS-305 (Nihon Emulsion Co., Ltd.)
*4 Product name: RHEOPEARL KL2 (Chiba Flour Milling Co., Ltd.)
*5 Product name: GHASSSOUL M (GHASSOUL JAPAN JAMIELA CO., LTD., Color tone: Dark green, Volume average particle diameter: 20 μm)
*6 Product name: KAOLIN JP-100 (Takehara Kagaku Kogyo Co., Ltd., Color tone: White, Volume average particle diameter: 11 μm)
*7 Product name: AEROSIL 200 Nippon Aerosil Co., Ltd.)
*8 Product name: AEROSIL RY200 (Nippon Aerosil Co., Ltd.)

As seen from the results shown in Table 1, the oil-based solid cleansing cosmetic of the present invention was excellent in properties required for a cleansing cosmetic such as makeup-removal property, washing-off property, and refreshing feeling after washing, and was also excellent in quality stability due to little powder sedimentation and color separation (see Examples 1 and 2). In particular, the cosmetic in which hydrophilic untreated silica was used as the fumed silica of the component (E) was even better excellent in washing-off property and refreshing feeling after washing. On the other hand, when the powder of the component (D) was not contained, the oil-based solid cleansing cosmetic was insufficient in makeup-removal property and refreshing feeling after washing (see Comparative Example 1). When the component (E), i.e. fumed silica was not contained, an oil-based solid cleansing cosmetic having a uniform dispersion of the powder could not be obtained due to a remarkable sedimentation of the powder (see Comparative Example 2). Further, in the case of using a dextrin palmitate that is a conventional thickener for an oil phase instead of the fumed silica, sedimentation of the powder could not be sufficiently prevented, and washing-off property and refreshing feeling after washing were also inferior (see Comparative Example 3).

Examples 3 to 5

(Oil-based Solid Cleansing Cosmetic)

An oil-based solid cleansing cosmetic of the formulation shown in table 2 was prepared according to the following production procedure. The obtained oil-based solid cleansing cosmetic was evaluated according to the methods described above as to makeup-removal property, washing-off property, refreshing feeling after washing, state of sedimentation of powder, and state of color separation. The evaluation results are shown in table 2.

(Production Procedure)

(1) Components 1 to 6 shown in Table 2 were heated to about 90° C. and mixed uniformly.

(2) Components 7 to 12 were added to the mixture prepared in the above (1), and then the resultant mixture was uniformly mixed at 90° C.

(3) The mixture prepared in the above (2) was filled in a jar container at 70° C. in a molten state, and then allowed to cool to obtain an oil-based solid cleansing cosmetic.

TABLE 2

|   | Component (%) | Example 3 | Example 4 | Example 5 |
|---|---|---|---|---|
| 1 | Polyethylene (※1) | 7.00 | 7.00 | 7.00 |
| 2 | Caprylic/capric triglyceride | Balance | Balance | Balance |
| 3 | Dicaprylyl carbonate | 12.00 | 12.00 | 12.00 |
| 4 | Purified water | 0.50 | 0.50 | 0.50 |
| 5 | PEG-20 glyceryl triisostearate (HLB: 10.4) (※2) | 12.00 | 12.00 | 12.00 |
| 6 | PEG-5 glyceryl triisostearate (HLB: 3) (※3) | 4.00 | 4.00 | 4.00 |
| 7 | Moroccan lava clay (※5) | 3.00 | 2.00 | |
| 8 | Mixture of clay, kaolin and mica (※9) | | 1.00 | 1.50 |
| 9 | Mixture of clay, montmolilonite, kaolin and mica (※10) | | | 1.50 |
| 10 | Silica (Specific surface area 200 m²/g) (※7) | 1.00 | 1.00 | 1.00 |
| 11 | Tocopherol | 0.05 | 0.05 | 0.05 |

TABLE 2-continued

|  | Component (%) | Example 3 | Example 4 | Example 5 |
|---|---|---|---|---|
| 12 | Phenoxyethanol | 0.20 | 0.20 | 0.20 |
| Evaluation | Makeup-removal Property | ◎ | ◎ | ◎ |
|  | Washing-off Property | ◎ | ◎ | ◎ |
|  | Refreshing Feeling After Washing | ◎ | ◎ | ◎ |
|  | State of Sedimentation of Powder | ○ | ○ | ○ |
|  | State of Color Separation | — | ◎ | ◎ |

*9 Product name: SPARCLAY SDR (TERRAMATER, Color tone: Dark red, Volume average particle size: 16 μm)
*10 Product name: SPARCLAY SG (TERRAMATER, Color tone: Green, Volume average particle size: 7 μm)

As seen from the results shown in Table 2, the oil-based solid cleansing cosmetic of the present invention was excellent in properties required for a cleansing cosmetic such as makeup-removal property, washing-off property, and refreshing feeling after washing, and was also excellent in quality stability due to little powder sedimentation. Further, even when natural clays having a bright color tone were used in combination, an oil-based solid cleansing cosmetic having a high commercial value due to being free of color separation could be obtained (see Examples 4 to 5).

Example 6

(Stick-Like Oil-Based Solid Cleansing Cosmetic)

An oil-based solid cleansing cosmetic of the formulation shown in table 3 was prepared according to the following production procedure. The obtained oil-based solid cleansing cosmetic was evaluated according to the methods described above as to makeup-removal property, washing-off property, refreshing feeling after washing, state of sedimentation of powder, and state of color separation. The evaluation results are shown in table 3.

(Production Procedure)
(1) Components 1 to 6 shown in Table 3 were heated to about 90° C. and mixed uniformly.
(2) Components 7 to 10 were added to the mixture prepared in the above (1), and then the resultant mixture was uniformly mixed at 90° C.
(3) The mixture prepared in the above (2) was filled in a stick-like container at 70° C. in a molten state, and then allowed to cool to obtain a stick-like oil-based solid cleansing cosmetic.

TABLE 3

|  | Component (%) | Example 6 |
|---|---|---|
| 1 | Polyethylene (✕1) | 12.00 |
| 2 | Caprylic/capric triglyceride | Balance |
| 3 | Dicaprylyl carbonate | 12.00 |
| 4 | Purified water | 0.50 |
| 5 | PEG-20 glyceryl triisostearate (HLB: 10.4) (✕2) | 14.00 |
| 6 | PEG-5 glyceryl triisostearate (HLB: 3) (✕3) | 6.00 |
| 7 | Medicinal carbon (✕11) | 0.50 |
| 8 | Silica (Specific surface area 300 m²/g) (✕12) | 1.00 |
| 9 | Tocopherol | 0.05 |
| 10 | Phenoxyethanol | 0.20 |
| Evaluation | Makeup-removal Property | ◎ |
|  | Washing-off Property | ◎ |
|  | Refreshing Feeling After Washing | ◎ |
|  | State of Sedimentation of Powder | ○ |
|  | State of Color Separation | — |

*11 Product name: MEDICINAL CARBON defined by Japanese pharmacopoeia (Color tone: Black, Volume average particle diameter: 39 μm) available from Nichi-Iko Pharmaceutical Co., Ltd.
*12 Product name: AEROSIL 300 available from Nippon Aerosil Co., Ltd.)

As seen from the results shown in Table 3, the oil-based solid cleansing cosmetic of Example 6 was excellent in cleansing property, and even when black medicinal carbon having an excellent adsorption effect was used, a stick-like oil-based solid cleansing cosmetic having a uniform appearance could be obtained.

INDUSTRIAL APPLICABILITY

According to the present invention, an oil-based solid cosmetic suitable for a cleansing cosmetic which is excellent in cleansing property, washing-off property and refreshing feeling after washing, and is also excellent in quality stability such as appearance and uniformity of composition is provided.

What is claimed is:

1. An oil-based solid cosmetic, consisting of:
(A) 3 to 15% by mass of a solid oil component having a melting point of 50 to 120° C., and comprising at least one selected from the group consisting of polyethylene wax, a Fischer-Tropsch wax, and a candelilla wax;
(B) 60 to 90% by mass of at least one selected from the group consisting of triethylhexanoin; diisostearyl malate; diglyceryl triisostearate; decaglyceryl decaisostearate; oligomeric ester of dimer acid and dimer diol; pentaerythrityl tetraisostearate; diglyceryl tetraisostearate; cetyl isooctanoate; isopropyl myristate; isopropyl palmitate; octyldodecyl myristate; neopentyl glycol dioctanoate; cholesterol fatty acid ester; and caprylic/capric triglyceride and dicaprylyl carbonate;
(C) 7 to 25% by mass of a nonionic surfactant having an HLB value of 5 to 13, and comprising polyoxyethylene fatty acid glyceryl and/or fatty acid polyoxyethylene alkyl ether;
(D) 0.2 to 15% by mass of a powder comprising a clay mineral having a volume average particle diameter of 2 to 100 μm or a carbon powder having a volume average particle diameter of 2 to 100 μm;
(E) 0.2 to 3% by mass of a fumed silica having a primary particle diameter of 20 nm or less and a specific surface area of 100 to 400 m²/g;
(F) water,
(G) tocopherol, and
(H) phenoxyethanol,
wherein the ratio by mass of the component (E) to the component (D) is 0.05 to 3, wherein the oil-based solid cosmetic is a cleansing cosmetic.

2. The oil-based solid cosmetic according to claim 1, wherein (B) is 60 to 90% by mass of caprylic/capric triglyceride and dicaprylyl carbonate.

* * * * *